United States Patent
Oikaze et al.

(10) Patent No.: US 9,241,388 B2
(45) Date of Patent: Jan. 19, 2016

(54) METHOD AND APPARATUS FOR MANUFACTURING A LIGHT-EMITTING DEVICE INCLUDING CORRECTION OF AN APPLICATION AMOUNT OF A FLUORESCENT RESIN BASED ON A FLUORESCENT PARTICLE CONCENTRATION

(75) Inventors: Hirotoshi Oikaze, Hyogo (JP);
Katsuyuki Nagahama, Hyogo (JP);
Kentaro Nishiwaki, Osaka (JP);
Yasuhiro Kabetani, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 64 days.

(21) Appl. No.: 13/700,145

(22) PCT Filed: May 11, 2012

(86) PCT No.: PCT/JP2012/003114
§ 371 (c)(1),
(2), (4) Date: Nov. 27, 2012

(87) PCT Pub. No.: WO2013/001707
PCT Pub. Date: Jan. 3, 2013

(65) Prior Publication Data
US 2013/0164865 A1    Jun. 27, 2013

(30) Foreign Application Priority Data
Jun. 29, 2011   (JP) ................. 2011-144019

(51) Int. Cl.
*B05C 11/00*   (2006.01)
*H05B 33/10*   (2006.01)
(Continued)

(52) U.S. Cl.
CPC ............ *H05B 33/10* (2013.01); *B05C 11/1005* (2013.01); *H01L 33/50* (2013.01);
(Continued)

(58) Field of Classification Search
CPC .. B05C 11/1005; B05B 12/084; G01N 21/62; G01N 21/64; G01N 2021/646; G01N 2021/6417; G01N 2021/6491; G01N 2021/6493; G01N 2021/6495; H05B 33/10; H01L 50/50; A61M 2205/3306
See application file for complete search history.

(56) References Cited

U.S. PATENT DOCUMENTS 4,979,824 A * 12/1990 Mathies et al. ............... 356/318
5,464,986 A * 11/1995 Boettcher et al. .......... 250/459.1
(Continued)

FOREIGN PATENT DOCUMENTS

| CN | 101995399 | 3/2011 |
|----|-----------|--------|
| EP | 1972926 | 9/2008 |

(Continued)

OTHER PUBLICATIONS

International Search Report issued Jul. 3, 2012 in International (PCT) Application No. PCT/JP2012/003114.
(Continued)

*Primary Examiner* — Dah-Wei D Yuan
*Assistant Examiner* — Karl Kurple
(74) *Attorney, Agent, or Firm* — Wenderoth, Lind & Ponack, L.L.P.

(57) ABSTRACT

A method of manufacturing a light-emitting device which includes a light-emitting source is provided by applying, onto the light-emitting source, a fluorescent resin which includes fluorescent particles and is stored in and discharged from an applicator. The method includes measuring a first concentration which is a concentration of the fluorescent particles included in the fluorescent resin discharged from the applicator; and applying, onto the light-emitting source, the fluorescent resin in an application amount determined based on the first concentration which has been measured and reference data which indicates a relationship between a concentration of the fluorescent particles and an application amount of the fluorescent resin that enables the light-emitting device to have constant chromaticity.

3 Claims, 8 Drawing Sheets

(51) Int. Cl.
*H01L 33/50* (2010.01)
*B05C 11/10* (2006.01)
*B05D 5/06* (2006.01)
*G01N 21/84* (2006.01)
*B05B 12/08* (2006.01)

(52) U.S. Cl.
CPC ............ *H01L 33/502* (2013.01); *B05B 12/084* (2013.01); *G01N 2021/8427* (2013.01); *H01L 2933/0041* (2013.01)

(56) References Cited

U.S. PATENT DOCUMENTS

| | | | | |
|---|---|---|---|---|
| 6,296,894 | B1 * | 10/2001 | Tanabe | C23C 14/243 118/708 |
| 6,579,563 | B1 | 6/2003 | Dillon | |
| 6,806,949 | B2 * | 10/2004 | Ludviksson et al. | 356/72 |
| 7,304,315 | B2 * | 12/2007 | Iketaki et al. | 250/461.2 |
| 7,477,764 | B2 * | 1/2009 | Haisch | 382/128 |
| 8,038,497 | B2 * | 10/2011 | Le Toquin | 445/25 |
| 8,253,117 | B2 * | 8/2012 | Gunji | 250/484.2 |
| 8,373,140 | B2 * | 2/2013 | Tokhtuev et al. | 250/461.1 |
| 8,509,867 | B2 * | 8/2013 | Workman et al. | 600/316 |
| 8,679,865 | B2 * | 3/2014 | Yoon et al. | 438/15 |
| 2004/0167742 | A1 * | 8/2004 | Haisch | 702/150 |
| 2005/0159068 | A1 * | 7/2005 | Noma et al. | 445/2 |
| 2006/0290924 | A1 * | 12/2006 | Iketaki et al. | 356/300 |
| 2007/0020181 | A1 * | 1/2007 | Workman et al. | 424/9.1 |
| 2009/0286335 | A1 | 11/2009 | Le Toquin | |
| 2010/0279575 | A1 | 11/2010 | Xu et al. | |
| 2011/0042581 | A1 | 2/2011 | Gunji | |
| 2011/0053295 | A1 | 3/2011 | Yoon et al. | |
| 2011/0213562 | A1 * | 9/2011 | Okawa | 702/19 |
| 2011/0260079 | A1 * | 10/2011 | Tokhtuev et al. | 250/461.1 |
| 2011/0281138 | A1 * | 11/2011 | Yoshioka | H01L 24/24 428/815 |
| 2012/0190136 | A1 * | 7/2012 | Hong | 438/7 |
| 2013/0323862 | A1 * | 12/2013 | Nonomura | H01L 22/10 438/15 |
| 2014/0080231 | A1 * | 3/2014 | Ikeuchi et al. | 438/7 |
| 2014/0212995 | A1 | 7/2014 | Yoon et al. | |

FOREIGN PATENT DOCUMENTS

| | | |
|---|---|---|
| JP | 2004-516925 | 6/2004 |
| JP | 2005-353649 | 12/2005 |
| JP | 2007-035951 | 2/2007 |
| JP | 2007179880 A * | 7/2007 |
| JP | 2009-010013 | 1/2009 |
| JP | 2009-272638 | 11/2009 |
| KR | 10-2011-0007705 | 1/2011 |
| KR | 10-2011-0070517 | 6/2011 |
| WO | 02/34417 | 5/2002 |

OTHER PUBLICATIONS

Office Action and Search Report issued Nov. 2, 2014 in corresponding Chinese Patent Application No. 2012280001058.7.

* cited by examiner

METHOD AND APPARATUS FOR MANUFACTURING A LIGHT-EMITTING DEVICE INCLUDING CORRECTION OF AN APPLICATION AMOUNT OF A FLUORESCENT RESIN BASED ON A FLUORESCENT PARTICLE CONCENTRATION

BACKGROUND OF INVENTION

1. [Technical Field]

The present invention relates to a method of manufacturing a light-emitting device which includes a light-emitting source such as a light emitting diode (LED) chip and to an apparatus for manufacturing such a light-emitting device.

2. [Background Art]

Conventionally, research and development has been conducted in various places on a light-emitting device which includes a LED chip that is a light-emitting source, and fluorescent particles as wavelength conversion materials (e.g., fluorescent pigment, and fluorescent dye) that are excited by light emitted from the LED chip and emit light different in color from the LED chip (for example, see Japanese Unexamined Patent Application Publication No. 2007-35951).

As such a light-emitting device, for example, a white light-emitting device (generally referred to as a white LED) which emits white light by combining a LED chip, which emits blue light or ultraviolet light, and fluorescent particles, which emit yellow light by converting a wavelength of blue light or a similar type of light, is commercially available.

Japanese Unexamined Patent Application Publication No. 2007-35951 describes, as shown in FIG. 9, an example of such a light-emitting device which includes: a LED chip 100, a mounting board 101 on which the LED chip 100 is mounted; a translucent sealing portion 102 which is in a semispherical shape and seals, on a mounting surface of the mounting board 101, the LED chip 100; a dome-shaped sealing member 103 which is formed to cover the translucent sealing portion 102 and fixed to the mounting board 101; and an air layer 104 formed between the translucent sealing portion 102 and the dome-shaped sealing member 103. The translucent sealing portion 102 includes fluorescent particles. The light-emitting device provides white light by using, as the LED chip 100, a GaN-based ultra-violet LED chip which emits ultraviolet light, and, as the fluorescent particles, red fluorescent particles, green fluorescent particles, and blue fluorescent particles.

Applying the light-emitting device shown in FIG. 9, a light-emitting device which provides white light by using, as the LED chip 100, a blue LED chip which emits blue light, and, as the fluorescent particles, yellow fluorescent particles is also conceivable.

The above-described light-emitting device is manufactured by applying, onto the LED chip 100, resin including fluorescent particles so that the fluorescent resin forms the translucent sealing portion 102.

When manufacturing the light-emitting device, there is a case where chromaticity of light emitted by the light-emitting device (hereinafter simply referred to as "chromaticity of light-emitting device") is not constant, which causes variation in the chromaticity of the manufactured light-emitting device. In view of this, as a light-emitting manufacturing apparatus which prevents occurrence of variation to chromaticity of the manufactured light-emitting device, a conventional manufacturing apparatus 105 shown in FIG. 10 is described in Japanese Unexamined Patent Application Publication No. 2004-516925.

The conventional manufacturing apparatus 105 includes: a syringe 106 which is for storing resin (fluorescent resin) including fluorescent particles; an air dispenser 107 which is for applying, onto the LED chip 100, fluorescent resin discharged from the syringe 106; a weight measurement unit 108 which measures a weight of the fluorescent resin discharged from the air dispenser 107; and a control unit 109 which causes the air dispenser 107 to discharge the fluorescent resin at a constant weight based on the value measured by the weight measuring unit 108.

The conventional manufacturing apparatus 105 employs, in order to manufacture a light-emitting device of constant chromaticity, a technique which allows the air dispenser 107 to discharge the fluorescent resin at a constant weight. It should be noted that chromaticity indicates chromaticity coordinates of the chromaticity diagram established by CIE (Commission Internationale de l'Eclairage).

SUMMARY OF INVENTION

Technical Problem

However, even when a light-emitting device is manufactured by discharging a constant weight of fluorescent resin from the air dispenser 107, there is a case where chromaticity of the manufactured light-emitting device does not be a constant value. Stated differently, the conventional manufacturing apparatus has a problem that variation occurs to the chromaticity of the light-emitting devices manufactured by the conventional manufacturing apparatus.

In view of the above, an object of the present invention is to solve the above-described problem and prevent occurrence of variation to chromaticity among the manufactured light-emitting devices.

Solution to Problem

A method of manufacturing a light-emitting device according to the present invention is a method of manufacturing a light-emitting device by applying, onto a light-emitting source, a fluorescent resin which includes fluorescent particles and is stored in and discharged from an applicator, the method includes: measuring a first concentration which is a concentration of the fluorescent particles included in the fluorescent resin discharged from the applicator; and applying, onto the light-emitting source, the fluorescent resin in an application amount determined based on the first concentration which has been measured and reference data which indicates a relationship between a concentration of the fluorescent particles and an application amount of the fluorescent resin that enables the light-emitting device to have constant chromaticity.

Furthermore, apparatus for manufacturing a light-emitting device according to the present invention is an apparatus for manufacturing a light-emitting device by applying, onto a light-emitting source, a fluorescent resin which includes fluorescent particles and is stored in and discharged from an applicator, the apparatus includes: a controller which controls an application amount of the fluorescent resin that is discharged from the applicator; a fluorescent particle measuring apparatus which measures a first concentration that is a concentration of the fluorescent particles included in the fluorescent resin discharged from the applicator; a storage in which reference data is stored beforehand, the reference data indicating a relationship between a concentration of the fluorescent particles and an application amount of the fluorescent resin that enables the light-emitting device to have constant chromaticity; and a correction apparatus which determines, based on the first concentration and the reference data, an application amount of the fluorescent resin to be applied onto the light-emitting source and notifies the controller of the determined application amount.

Advantageous Effects of Invention

The present invention makes it possible to prevent occurrence of variation to chromaticity among the manufactured light-emitting devices.

DETAILED DESCRIPTION OF EMBODIMENT

Figure 1:
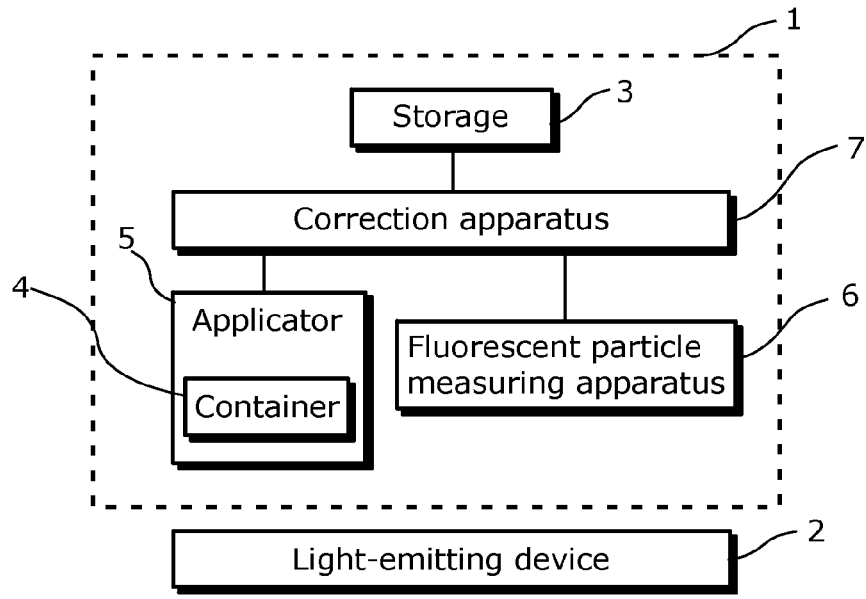
FIG. 1 is a block diagram showing a structure of an apparatus for manufacturing a light-emitting device according to an embodiment.

The following describes an embodiment of the present invention with reference to the drawings. It should be noted that the embodiment described below merely shows examples of a method of manufacturing a light-emitting device and an apparatus for manufacturing a light-emitting device according to the present invention. Therefore, the present invention is defined by words in the claims with reference to the below embodiment and by no means limited to the below embodiment.

Embodiment

First, an outline of an apparatus structure of a manufacturing apparatus 1 for manufacturing a light-emitting device according to an embodiment shown in FIG. 1 (hereinafter simply referred to as "manufacturing apparatus 1") is described.

The manufacturing apparatus 1 includes: a storage 3 which stores reference data; a container 4 which stores fluorescent resin which is a resin including fluorescent particles of a known concentration; an applicator 5 which causes a predetermined amount of fluorescent resin to be discharged from the container 4 and applies the fluorescent resin onto a light-emitting device 2; and a fluorescent particle measuring apparatus 6 which measures, at predetermined time intervals, a concentration of fluorescent particles included in the fluorescent resin discharged from the container 4. Here, the reference data is data which indicates a relationship between a concentration of fluorescent particles included in the fluorescent resin, an amount of fluorescent resin applied, and chromaticity of the light-emitting device 2. The manufacturing apparatus 1 further includes a correction apparatus 7 which notifies, based on the measured concentration of the fluorescent particles and the reference data stored in the storage 3, the applicator 5 of an amount of the fluorescent resin to be applied so that the light-emitting device 2 has desired chromaticity.

With the above-described structure, even when the concentration of the fluorescent particles included in the fluorescent resin discharged from the container 4 varies over time, the manufacturing apparatus 1 can apply, onto the light-emitting device 2, fluorescent resin in an amount suitable for the concentration of the fluorescent particles included in the fluorescent resin. Therefore, the light-emitting devices 2 can be stably manufactured, by reducing occurrence of variation to chromaticity among the manufactured light-emitting devices 2.

The outline of the manufacturing apparatus 1 is as described above. Here, before describing the manufacturing apparatus 1 in detail, the light-emitting device 2 manufactured by the manufacturing apparatus 1 is described.

Figure 2:
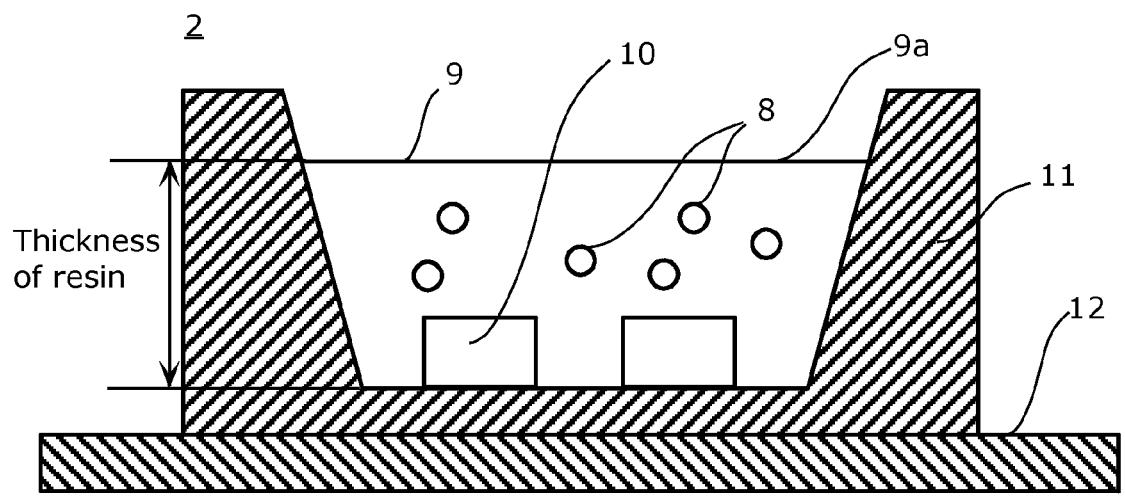
FIG. 2 is a schematic diagram showing a structure of the light-emitting device which is manufactured by the apparatus for manufacturing the light-emitting device according to the embodiment.

FIG. 2 is a schematic diagram of the light-emitting device 2. The light-emitting device 2 includes: a fluorescent resin 9 which includes fluorescent particles 8; and a LED chip 10 which is a light-emitting source and is sealed by the fluorescent resin 9. The light-emitting device 2 further includes a package 11 which has a recess. The diameter of the recess decreases toward the bottom portion of the recess. The LED chip 10 is placed on the bottom portion of the recess of the package 11. Furthermore, the recess of the package 11 is filled with the fluorescent resin 9. The LED chip 10 is sealed in the package 11 by the fluorescent resin 9. In addition, the package 11 is fixed to a board 12 on which a circuit pattern is formed. The LED chip 10 is connected to the circuit pattern on the board 12 via the package 11.

It should be noted that, besides the LED chip 10, the light-emitting source may be a plasma light-emitting source or a similar type of light-emitting source.

In this embodiment, a blue LED chip which emits blue light is used as the LED chip 10. Furthermore, yellow fluorescent particles, which emit yellow light when blue light is received, are used as the fluorescent particles 8. With the LED chip 10 and the fluorescent particles 8, the light-emitting device 2 becomes the white LED which emits white light. It should be noted that, as another structure of the white LED, the light-emitting device 2 may be configured of an ultraviolet LED chip which emits ultraviolet light and three types of fluorescent particles 8 each of which emits one of red, green, and blue light when receiving the ultraviolet light.

Furthermore, as the board 12, a flat plate made from aluminum, nickel, glass epoxy, or a similar material which has heat dissipating capability and rigidity is used. The package 11 is formed of resin such as polybutylene terephthalate, polyphthalamide, polycarbonate, or a similar material. The resin which is a base material of the fluorescent resin 9 is translucent resin at least to visible light, and is formed of thermosetting resin such as a silicone resin, an epoxy resin, or a similar material. Specifically, the fluorescent resin 9 is obtained, by adding the fluorescent particles 8 to the above-described resins.

Next, a method of manufacturing the light-emitting device 2 is described.

First, the package 11 is fixed on the board 12. Next, using solder or conductive paste, the LED chip 10 is placed in the recess of the package 11 so that the LED chip 10 is electrically connected to the circuit pattern on the board 12. Subsequently, the fluorescent resin 9 is applied to the recess of the package 11 in such a manner that the LED chip 10 is covered. Lastly, heat is applied so that the fluorescent resin 9 is cured. The LED chip 10 is thus sealed by the fluorescent resin 9. The light-emitting device 2 is thus manufactured.

The above is the description of the light-emitting device 2 which is manufactured by the manufacturing apparatus 1 shown in FIG. 1. The following describes the applicator 5 included in the manufacturing apparatus 1 according to this embodiment.

Figure 3:
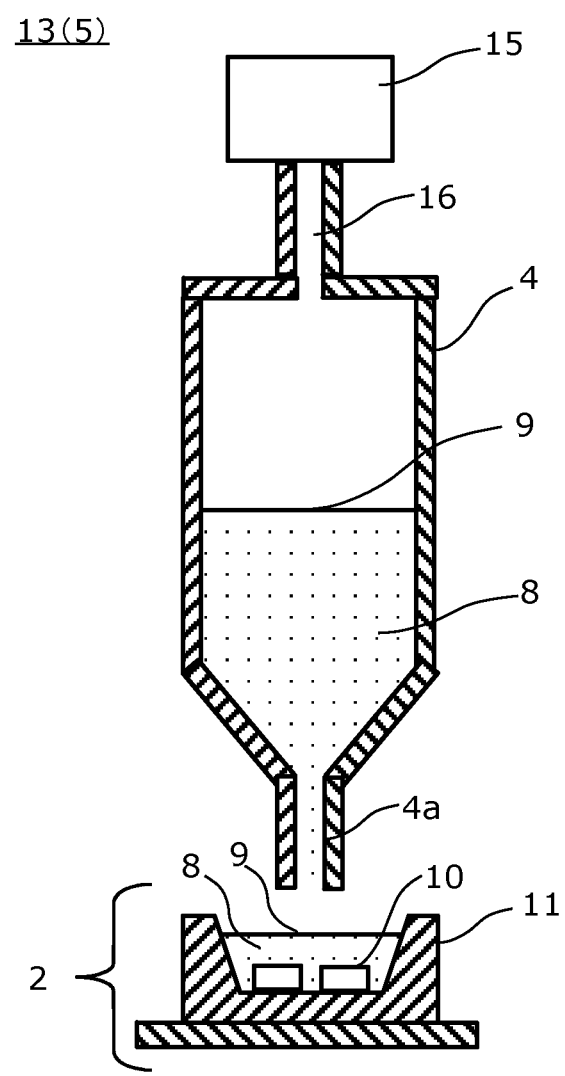
FIG. 3 is a schematic diagram showing a structure of an applicator according to the embodiment.

The applicator 5 shown in FIG. 1 is an apparatus which is for applying the fluorescent resin 9 to the LED chip 10 in FIG. 2. Here, an air dispenser 13 shown in FIG. 3 is used as the applicator 5.

Here, a structure of the air dispenser 13 is described.

The air dispenser 13 includes: the container 4 which is for storing the fluorescent resin 9 including the fluorescent particles 8; and a controller unit 15 which adjusts the amount of the fluorescent resin 9 discharged from the container 4 by controlling air supplied into the container 4. The container 4 has an outlet 4a through which the fluorescent resin 9 is discharged. The light-emitting device 2 which includes the LED chip 10 is disposed vertically below the outlet 4a.

The controller unit 15 includes a precision regulator, a precision digital timer, or a similar type of unit. The controller unit 15 supplies, into the container 4 through an air tube 16, air of which pressure and pressing time is controlled. This allows the air dispenser 13 to discharge a desired amount of fluorescent resin 9. Furthermore, the controller unit 15 is controlled by an after-mentioned controller 5a shown in FIG. 11 on the pressure and the pressing time at the time of the discharge of the fluorescent resin 9 shown in FIG. 3.

It should be noted that, instead of the air dispenser 13, a jet dispenser or a screw dispenser may be used as the applicator 5. Any apparatus may be used as the applicator 5 as long as the apparatus can control the amount of the fluorescent resin 9 discharged from the container 4.

Here, the relationship between a concentration of the fluorescent particles 8 included in the fluorescent resin 9, an amount of the fluorescent resin 9 applied, and chromaticity of the light-emitting device 2 is described.

The inventors performed experimental manufacturing, simulation, and the like repeatedly, and found that chromaticity of the light-emitting device 2 depends on a concentration of the fluorescent particles 8 included in the applied fluorescent resin 9 (hereinafter simply referred to as a "concentration of the fluorescent particles 8").

Furthermore, through dedicated study further conducted, the inventors found that chromaticity of the light-emitting device 2 depends on a thickness of the applied fluorescent resin 9 (a height from the bottom portion of the recess of the package 11 shown in FIG. 2 to a surface 9a of the fluorescent resin 9 (see FIG. 2), which is hereinafter simply referred to as a thickness of the fluorescent resin 9). It should be noted that the thickness of the fluorescent resin 9 is a value determined by an amount of the fluorescent resin 9 to be applied and design information of the light-emitting device 2 such as a shape of the package 11, a disposition of the LED chip 10, and the like. When the design information of the light-emitting device 2 is constant, it is possible to make the thickness of the fluorescent resin 9 constant by making the amount of the applied fluorescent resin 9 constant.

From these findings, as the relationship between the concentration of the fluorescent particles 8, the amount of the applied fluorescent resin 9, and chromaticity of the light-emitting device 2, the inventors presumed that, as long as the concentration of the fluorescent particles 8 and the thickness of the fluorescent resin 9 (an amount of the applied fluorescent resin 9) is constant, chromaticity of the manufactured light-emitting device 2 is also constant.

However, through further experiments, the inventors found that the concentration of the fluorescent particles 8 included in the fluorescent resin 9 which is discharged from the applicator 5 varies over time (concentration variation phenomenon). In other words, the inventors found that, even when the thickness of the fluorescent resin 9 (amount of the applied fluorescent resin 9) is constant, the manufactured light-emitting devices 2 have different chromaticity because of the variation in concentration of the fluorescent particles 8. The concentration variation phenomenon occurs even when the fluorescent resin 9 is not newly put into the applicator 5. In other words, the concentration variation phenomenon is a phenomenon which occurs between when the fluorescent resin 9 is put into the applicator 5 and when the fluorescent resin 9 is newly put into the applicator 5.

Here, the reason why the concentration variation phenomenon occurs is described with reference to FIG. 3. The fluorescent particles 8 have specific gravity that is greater than specific gravity of resin included in the fluorescent resin 9. In this embodiment, specific gravity of the fluorescent particles 8 is 4.5, and specific gravity of the resin included in the fluorescent resin 9 is 1.0. The difference in specific gravity causes the fluorescent particles 8 to settle out over time in the fluorescent resin 9 in the container 4. As such, over time, the concentration of the fluorescent particles 8, which is included in the fluorescent resin 9 discharged from the container 4, is increased due to the settling as compared to an initial state. The initial state refers to the concentration of the fluorescent particles 8 at the point in time when the discharge of the fluorescent resin 9 from the container 4 is started (a point in time when the fluorescent resin 9 is put into the container 4 and manufacturing of the light-emitting device 2 is started).

As mentioned before, chromaticity of the light-emitting device 2 varies when the concentration of the fluorescent particles 8 varies. In other words, there is a case where chromaticity of the light-emitting device 2 manufactured at a certain time $t_1$ and chromaticity of the light-emitting device 2 manufactured at a time $t_2$, which is a point in time after an elapse of a predetermined period of time from the time $t_1$, are uneven. When it is assumed that the light-emitting device 2 is a white LED and the light-emitting device 2 is manufactured by always applying a constant amount of the fluorescent resin 9, there may be a case where chromaticity of the light-emitting device 2 varies depending on the time of manufacturing and yellowish light or bluishness light is produced. The light-emitting device 2 which produces yellowish light or a similar color of light is handled as a defective item. Thus, occurrence of yellowishness or a similar color, that is, variations in chromaticity of the light-emitting devices 2 need to be reduced when manufacturing the light-emitting devices 2.

In view of this, the inventors adopted a method in which the amount of the fluorescent resin 9 to be applied (to be discharged from the container 4) is corrected according to the variation in concentration of the fluorescent particles 8, which occurs over time, so that the chromaticity of the manufactured light-emitting device 2 is constant. One of the factors that cause variation in chromaticity of the light-emitting device 2 is a concentration of the fluorescent particles 8, which varies over time during the manufacturing of the light-emitting device 2 but is difficult to make adjustment according to the variation. Thus, the other of the factors that causes variation in chromaticity of the light-emitting device 2, which is the thickness of the fluorescent resin 9, is corrected. In other words, the thickness of the fluorescent resin 9 depends on the amount of the applied fluorescent resin 9, and thus the amount of the fluorescent resin 9 to be applied is corrected to allow the chromaticity of the light-emitting device 2 to be constant.

The following describes details of the method of correcting the amount of the fluorescent resin 9 to be applied according to the variation in concentration of the fluorescent particles 8, which occurs over time, so that the manufactured light-emitting device 2 has a constant chromaticity.

First, a reference table is prepared in order to know how the amount of the fluorescent resin 9 to be applied should be corrected when a variation occurs in concentration of the fluorescent particles 8. The reference table shows, in a form of a data table, reference data which is obtained by measuring in advance the relationship between the concentration of the fluorescent particles 8, the amount of the applied fluorescent resin 9, and the chromaticity of the light-emitting device 2. In other words, the relationship between the concentration of the fluorescent particles 8 and the application amount of the fluorescent resin 9 which allows chromaticity of the light-emitting device 2 to be constant is stored in the storage 3 in advance as the reference table.

Here, the reference table is described with a specific example. An example of the reference table is shown in Table 1. It should be noted that the white LED expresses white light by color mixture of blue light and yellow light. The value of chromaticity of the white LED is a value on the line segment which connects blue and yellow on a chromaticity diagram. In the chromaticity (X,Y), determining one of the coordinates in the chromaticity diagram also determines the other of the coordinates. Therefore, here, only X coordinate of chromaticity is described. Furthermore, in Table 1, as a unit of concentration, a mass percentage is used, and, instead of an amount of the applied fluorescent resin 9, a thickness of the fluorescent resin 9 is shown.

TABLE 1

|  |  | Fluorescent particle concentration | | |
| --- | --- | --- | --- | --- |
|  |  | 4 wt % | 5 wt % | 6 wt % |
| Thickness of resin | 0.5 mm | 0.275 | 0.285 | 0.295 |
|  | 0.6 mm | 0.285 | 0.295 | 0.305 |
|  | 0.7 mm | 0.295 | 0.305 | 0.315 |

Table 1 shows reference data which is a relationship between the thickness of the fluorescent resin 9 ("thickness of resin" in Table 1), a concentration of the fluorescent particles 8, and chromaticity of the light-emitting device 2. In Table 1, when the thickness the fluorescent resin 9 is 0.5 mm and the concentration of the fluorescent particles 8 is 4 wt %, 5 wt %, and 6 wt %, chromaticity of the light-emitting device 2 is 0.275, 0.285, and 0.295, respectively. Furthermore, when the thickness the fluorescent resin 9 is 0.6 mm and the concentration of the fluorescent particles 8 is 4 wt %, 5 wt %, and 6 wt %, chromaticity of the light-emitting device 2 is 0.285, 0.295, and 0.305, respectively. Furthermore, when the thickness the fluorescent resin 9 is 0.7 mm and the concentration of the fluorescent particles 8 is 4 wt %, 5 wt %, and 6 wt %, chromaticity of the light-emitting device 2 is 0.295, 0.305, and 0.315, respectively.

Next, a technique for correcting the amount of the fluorescent resin 9 to be applied using Table 1 is described. For example, it is assumed that the thickness of the fluorescent resin 9 applied onto the LED chip 10, which is a first light source, is 0.6 mm and the concentration of the fluorescent particles 8 is 5 wt % at the time $t_1$ that is immediately after the air dispenser 13 in FIG. 3 starts application. According to table 1, chromaticity of the light-emitting device 2 manufactured at the time $t_1$ is 0.295. On the other hand, the case is considered in which the concentration of the fluorescent particles 8 in the air dispenser 13 in FIG. 3 is 6 wt % at the time $t_2$, which is after an elapse of one hour from the time $t_1$, due to the effect of settling out. At the time $t_2$, when it is assumed that the thickness of the fluorescent resin 9 applied onto the LED chip 10, which is a third light source, is 0.6 mm as with at the time $t_1$, chromaticity of the light-emitting device 2 is 0.305. In other words, variation occurs in chromaticity as compared to the light-emitting device 2 manufactured one hour earlier. In view of this, the amount of the fluorescent resin 9 applied from the air dispenser 13 onto the LED chip 10, which is a second light source, is adjusted so that the thickness of the fluorescent resin 9 is 0.5 mm at the time $t_2$ and onward. Then, chromaticity of the light-emitting device 2 is 0.295 according to Table 1, and thus the chromaticity is the same as the light-emitting device 2 manufactured one hour earlier.

In other words, assuming that there is a case in which, as a condition that allows the light-emitting device 2 to have a specific chromaticity $X_1$, a first amount (a first application amount) of the fluorescent resin 9 which includes the fluorescent particles 8 at first concentration is applied onto the first light source. Furthermore, assuming that there is a case in which, as another condition that allows the light-emitting device 2 to have the same chromaticity $X_1$, a second amount (a second application amount) of the fluorescent resin 9 which includes the fluorescent particles 8 at second concentration is applied onto the second light source. Further, it is assumed that the first amount of the fluorescent resin 9 which includes the fluorescent particles 8 at the first concentration is applied onto the first light source from the air dispenser 13 at the time $t_1$. Then, it is assumed that, at the time $t_2$, the concentration of the fluorescent particles 8 included in the fluorescent resin 9 applied onto the third light source by the air dispenser 13 changes to the second concentration. In this case, at the time $t_2$ and onward, the amount of the fluorescent resin 9 applied onto the second light source is the second amount instead of the first amount. With this, it is possible to allow chromaticity of the light-emitting device 2 manufactured at the time $t_1$ and chromaticity of the light-emitting device 2 manufactured at the time $t_2$ and onward to agree with a first chromaticity. It should be noted that the first concentration and the second concentration are different concentrations, and the first amount and the second amount are different amounts.

Here, for the sake of description, representative values are shown in Table 1 as discrete data. On the other hand, the inventors found that linear relationship (linear function relationship) exists between the concentration of the fluorescent particles 8 and the thickness of the fluorescent resin 9 (amount of the applied fluorescent resin 9) which make it possible to obtain specific chromaticity. A specific example of the linear relationship is described using a graph shown in FIG. 4.

Figure 4:
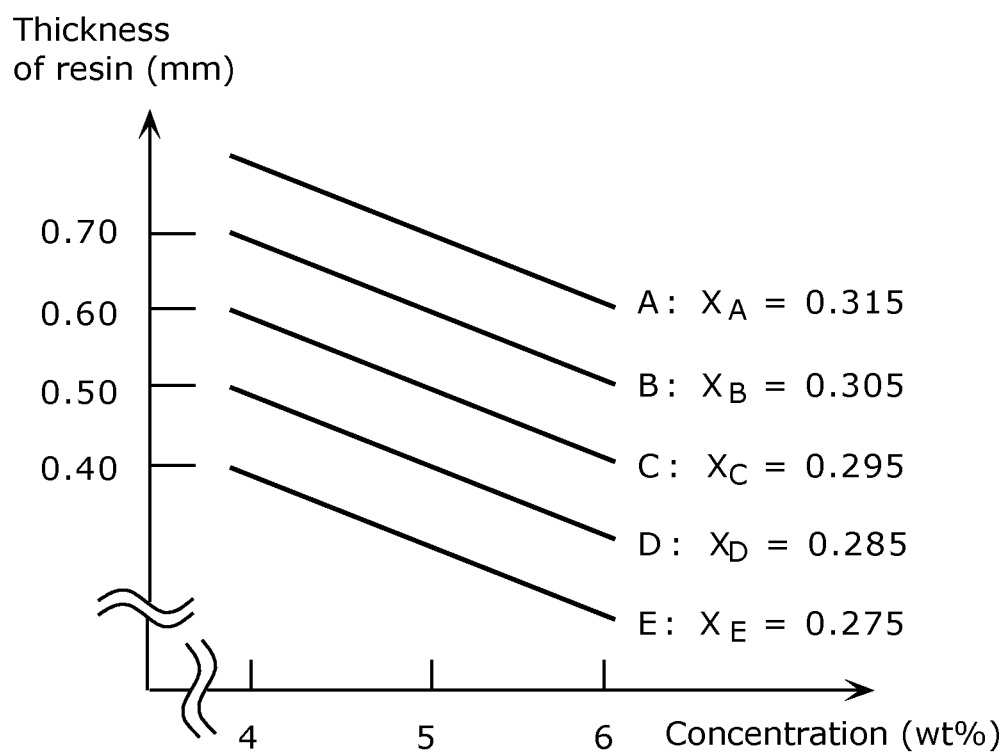
FIG. 4 is a diagram showing a graph which shows a relationship between a thickness of a fluorescent resin, a concentration of fluorescent particles, and chromaticity of the light-emitting device.

In FIG. 4, the vertical axis indicates a thickness of the fluorescent resin 9 (mm) ("thickness of resin" in FIG. 4) and the horizontal axis indicates a concentration of the fluorescent particles 8 (wt %). Furthermore, in FIG. 4, a line A indicates a relationship between the thickness of the fluorescent resin 9 and the concentration of the fluorescent particles 8 which satisfies $X_A$=0.315 and a line B indicates a relationship between the thickness of the fluorescent resin 9 and the concentration of the fluorescent particles 8 which satisfies $X_B$=0.305, where each of $X_A$ and $X_B$ represents chromaticity of the light-emitting device 2. In addition, a line C indicates a relationship between the thickness of the fluorescent resin 9 and the concentration of the fluorescent particles 8 which satisfies $X_C$=0.295, a line D indicates a relationship between the thickness of the fluorescent resin 9 and the concentration of the fluorescent particles 8 which satisfies $X_D$=0.285, and a line E indicates a relationship between the thickness of the fluorescent resin 9 and the concentration of the fluorescent particles 8 which satisfies $X_E$=0.275, where each of $X_C$, $X_D$, and $X_E$ represents chromaticity of the light-emitting device 2.

Based on the linear relationship shown in FIG. 4, it is possible to correct the amount of the fluorescent resin 9 to be applied so that chromaticity of the light-emitting device 2 does not vary even when the concentration of the fluorescent particles 8 varies. It should be noted that the thickness of the fluorescent resin 9 is a value determined by the amount of the applied fluorescent resin 9. In other words, as the reference data, the relationship between the concentration of the fluorescent particles 8, the amount of the applied fluorescent resin 9, and chromaticity of the light-emitting device 2 is associated with the function as shown in FIG. 4 and stored in the storage 3. With this, it is possible to select, from the reference data, the application amount of the fluorescent resin according to the concentration of the fluorescent particles 8 and correct the amount of the fluorescent resin 9 to be applied with high precision so that the manufactured light-emitting device 2 has constant chromaticity.

The technique for correcting the amount of the applied fluorescent resin 9 using the reference data is as described above. It should be noted that, to manufacture the light-emitting device 2 which has constant chromaticity, in the manufacturing apparatus 1 shown in FIG. 1, the applicator 5 determines, based on a notification from a correction apparatus 7, the amount of the fluorescent resin 9 to be applied. Specifically, the correction apparatus 7 corrects, according to the concentration of the fluorescent particles 8, the amount of the fluorescent resin 9 discharged from the applicator 5. Furthermore, the reference data is stored in the storage 3, and, based on the reference data stored in the storage 3, the correction apparatus 7 corrects the amount of the fluorescent resin 9 to be applied.

It should be noted that the maximum amount of the applied fluorescent resin 9 is an amount which does not cause the fluorescent resin 9 to flow out of the package 11 shown in FIG. 2. This is because the appearance of a product is damaged if the fluorescent resin 9 adheres to an outside of the package 11. Furthermore, the minimum amount of the applied fluorescent resin 9 is an amount with which the thickness of the fluorescent resin 9 is twice as thick as the height (distance from the package 11 in the vertical direction) of the LED chip 10. This amount is required to seal the LED chip 10.

Next, a fluorescent particle measuring apparatus 6 which is shown in FIG. 1 and measures the concentration of the fluorescent particles 8 is described.

The fluorescent particles 8 included in the fluorescent resin 9 settles out over time. The concentration of the fluorescent particles 8 in the fluorescent resin 9, which is discharged from the applicator 5, varies over time. The amount of variation in concentration of the fluorescent particles 8 over time is determined by the following: a relationship between a specific gravity of the fluorescent particles 8 and a specific gravity of the fluorescent resin 9; and application condition, such as temperature at the time of application. Thus, the amount of variation in the concentration of the fluorescent particles 8 over time can be estimated in advance. However, there may be a case where the concentration of the fluorescent particles 8 does not vary according to the estimated variation amount. Thus, if the amount of the applied fluorescent resin 9 is corrected based only on the estimated variation amount, it is not possible to mass produce the light-emitting devices 2 of chromaticity having no variations.

In view of this, the manufacturing apparatus 1 shown in FIG. 1 includes a fluorescent particle measuring apparatus 6 which is for measuring concentration of the fluorescent particles 8 applied from the air dispenser 13 that is an applicator. The correction apparatus 7 refers to, based on the concentration of the fluorescent particles 8 measured by the fluorescent particle measuring apparatus 6, the reference data stored in the storage 3, and causes the applicator 5 to apply the corrected amount of the fluorescent resin 9.

Note that it takes, depending on the application condition, a few tens of minutes to a few hours before variation due to the settling occurs in the concentration of the fluorescent particles 8. During that time, the fluorescent particle measuring apparatus 6 does not have to constantly operate. It is sufficient that the fluorescent particle measuring apparatus 6 measure the concentration of the fluorescent particles 8 at predetermined time intervals which is set beforehand.

Here, a method of setting the predetermined time intervals is described. For example, it is assumed that the range of chromaticity required for the light-emitting device 2 to be a good item is 0.285 to 0.305. In addition, it is assumed that, at the time $t_1$, the concentration of the fluorescent particles 8 is 4 wt % and the fluorescent resin 9 in an amount that allows the thickness of the fluorescent resin 9 to be 0.6 mm is applied. Note that, in this case, Table 1 shows that chromaticity of the manufactured light-emitting device 2 is 0.285. In addition, it is assumed that the concentration of the fluorescent particles 8 at the time $t_2$ that is one hour after the time $t_1$ is 6 wt %. In this case, the predetermined time period may be one hour, and the concentration of the fluorescent particles 8 may be measured once every one hour. Table 1 shows that, when the concentration of the fluorescent particles 8 is 6 wt % and the thickness of the fluorescent resin is 0.6 mm, the chromaticity of the manufactured light-emitting device 2 is 0.305. In other words, even when the same amount of the fluorescent resin 9 is applied continuously for one hour, chromaticity of the manufactured light-emitting device 2 falls within a range of a good item. However, to be on the safe side so that defective item is not manufactured, it is preferable that the predetermined time period be set to 30 minutes, the concentration of the fluorescent particles 8 be measured once every 30 minutes, and the amount of the fluorescent resin 9 to be applied be corrected. Specifically, the predetermined time period is determined beforehand based on the range of chromaticity required for the light-emitting device 2 to be a good item and a rate of change in concentration of the fluorescent particles 8. Furthermore, another definition of the predetermined time period is a time period during which the same amount of the fluorescent resin 9 can be continuously applied without having the chromaticity of the manufactured light-emitting device 2 falling outside a range of a good item, even when the concentration of the fluorescent particles 8 varies. At every time intervals that is set beforehand as the predetermined time period described above, the fluorescent particle measuring apparatus 6 measures concentration of the fluorescent particles 8. It should be noted that the predetermined time period is stored in the storage 3.

Figure 5:
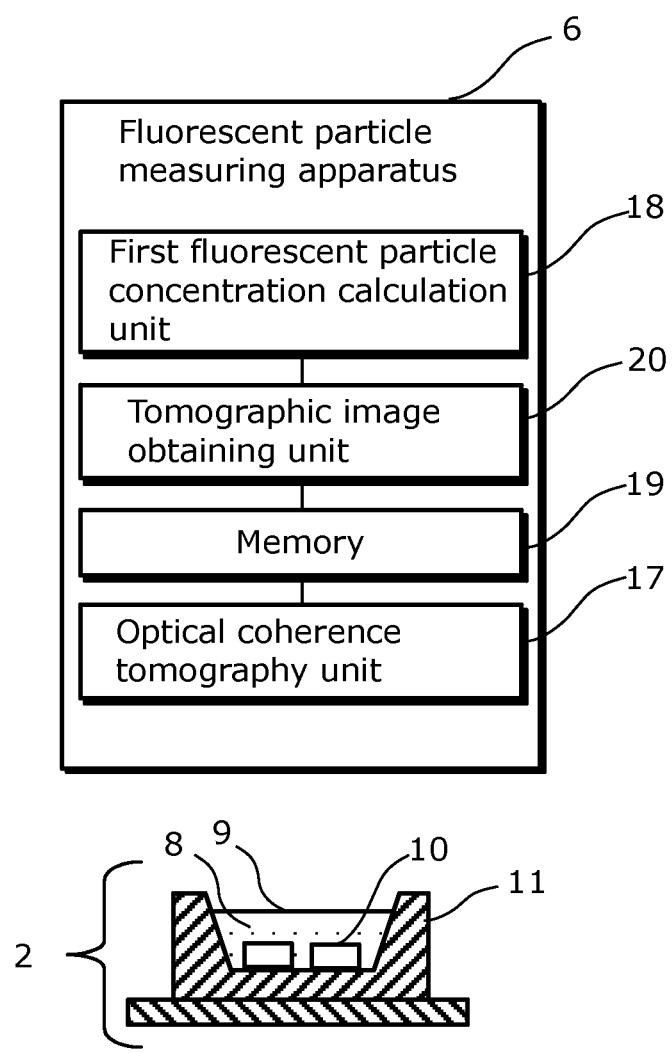
FIG. 5 is a schematic diagram showing a structure of a fluorescent particle measuring apparatus according to the embodiment.

Here, a specific structure of the fluorescent particle measuring apparatus 6 is described using FIG. 5.

The fluorescent particle measuring apparatus 6 shown in FIG. 5 includes: an optical coherence tomography unit 17 which obtains information on an internal structure of the fluorescent resin 9 applied onto the LED chip 10; and a first fluorescent particle concentration calculation unit 18 (a first concentration calculation unit) which calculates the concentration of the fluorescent particles 8 based on the obtained information on the internal structure.

The optical coherence tomography unit 17 employs a technique of optical coherence tomography (OCT). The optical coherence tomography unit 17 is a unit which irradiates measurement light via a polygon mirror, a galvanometer mirror, or a similar type of mirror (hereinafter referred to as a "sweeping unit") and obtains, as a three-dimensional tomographic image, the internal structure of the fluorescent resin 9 applied onto the LED chip 10. It should be noted that the three-dimensional tomographic image is obtained as follows. First, the information on the internal structure (internal structure information), which is obtained by the optical coherence tomography unit 17 at each of sweeping positions in the fluorescent resin 9 using the sweeping unit, is stored in a memory 19 together with the corresponding information on the sweeping position (position information). Next, the stored internal structure information is rearranged according to the position information by a tomographic image obtaining unit 20. A three-dimensional tomographic image is thus obtained. It should be noted that, the measurement light irradiated from the optical coherence tomography unit 17 is reflected off the fluorescent resin 9, the fluorescent particles 8, and the package 11, and thus the obtained three-dimensional tomographic image includes, as the information on the internal structure, the information on such reflected light. Here, the optical coherence tomography unit may include the optical coherence tomography unit 17, the memory 19, and the tomographic image obtaining unit 20.

Next, a technique for measuring a concentration of the fluorescent particles 8 by the fluorescent particle measuring apparatus 6 is described.

The first fluorescent particle concentration calculation unit 18 performs noise elimination and binarization on the obtained three-dimensional tomographic image to detect a position of the surface of the fluorescent resin 9, positions of the fluorescent particles 8, and the shape of the package 11. Next, based on the detected information, the first fluorescent particle concentration calculation unit 18 calculates the volume of the applied fluorescent resin 9 and counts the number of the fluorescent particles 8. Based on the volume of the fluorescent resin 9 and the number of the fluorescent particles 8, number concentration of fluorescent particle per unit volume is calculated by dividing N by V as shown in (Math. 1), where N represents the number of the fluorescent particles 8 and V represents the volume of the applied fluorescent resin 9.

[Math. 1]

$$C = \frac{N}{V} \quad \text{(Math. 1)}$$

In this manner, with the fluorescent particle measurement unit, the concentration of the fluorescent particles 8 is obtained. It should be noted that, instead of calculating the number concentration using (Math. 1), a percent by mass concentration of the fluorescent particles may be obtained based on an average mass of the fluorescent particles 8 and a mass of the fluorescent resin 9 per unit volume.

Here, signals of the light reflected off the fluorescent particles 8 are represented by a Gaussian function. Thus, the signal is binarized, pulsed, and counted to obtain the number of the fluorescent particles 8. It should be noted that, utilizing the characteristic that the sum of light intensities of light reflected off the fluorescent particles 8 is proportional to the concentration, the relationship between the concentration and the light intensity of the reflected light may be prepared beforehand as a table. The concentration of the fluorescent particles 8 may be calculated based on the prepared table and the detected light intensity of the reflected light.

It should be noted that it is preferable that the measurement light used by the optical coherence tomography unit 17 have a wavelength which is not absorbed by the fluorescent resin 9 and does not excite the fluorescent particles 8. This is because if the wavelength of the measurement light excites the fluorescent particles 8, accuracy for detecting the internal structure decreases. Specifically, it is preferable that the measurement light has a wavelength greater than or equal to 500 nm.

Furthermore, as the size of the fluorescent particles 8 is about 10 to 20 μm, it is preferable that the resolution of the optical coherence tomography unit 17 be 10 μm or less.

It should be noted that the optical coherence tomography unit 17 employs a technique of swept source OCT (SS-OCT), that is, the wavelength of the irradiated measurement light is continuously changed to obtain a tomographic image. Alternatively, the optical coherence tomography unit 17 may employ a technique of spectral domain OCT (SD-OCT) in which measurement lights of different wavelengths are simultaneously irradiated and the light reflected off the object is dispersed to obtain a tomographic image.

Figure 6:
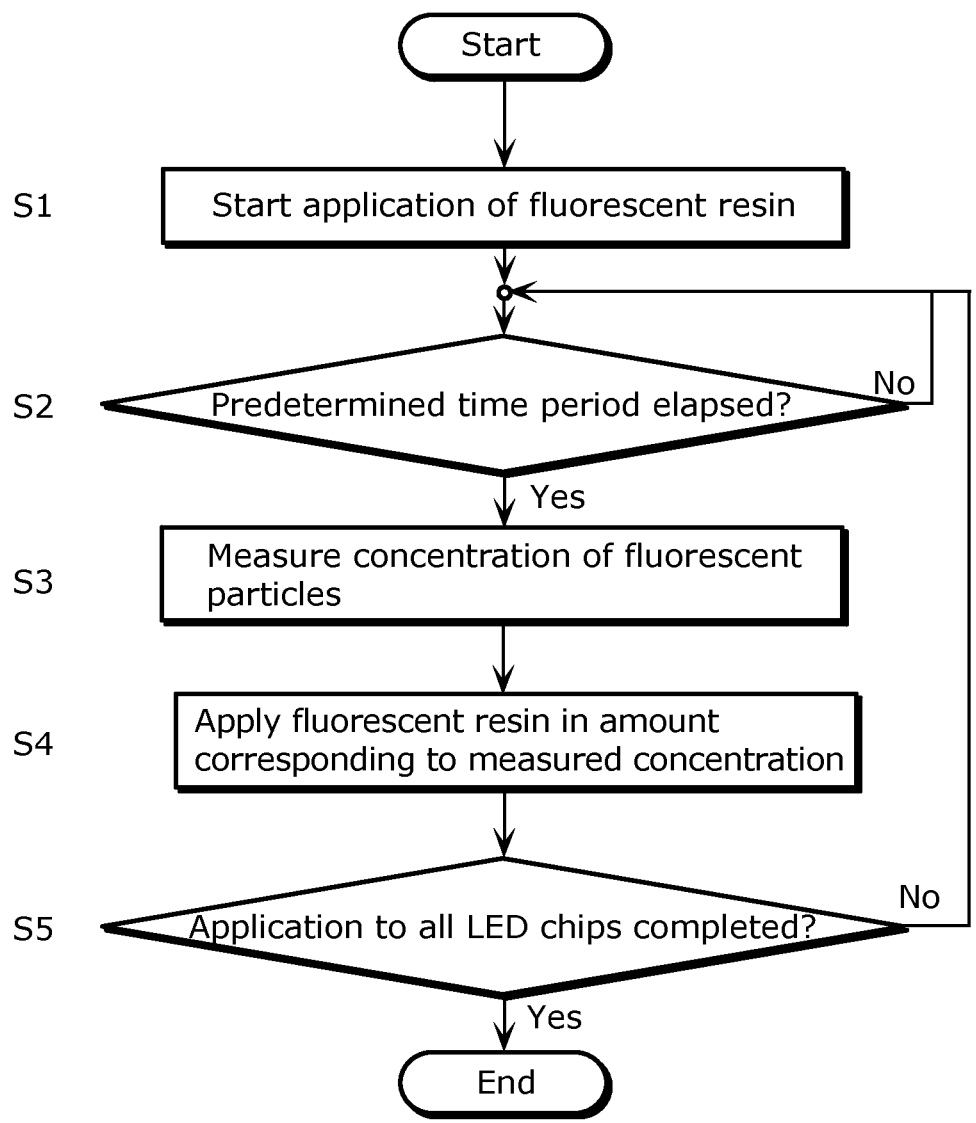
FIG. 6 is a flowchart showing operations of the apparatus for manufacturing the light-emitting device according to the embodiment.

FIG. 6 is a flowchart showing an operation performed by the above-described manufacturing apparatus 1 shown in FIG. 1 when manufacturing the light-emitting device 2 shown in FIG. 2. The flowchart shown in FIG. 6 is described using FIG. 1 and FIG. 2.

In Step S1, the applicator 5 is caused to discharge the fluorescent resin 9 including the fluorescent particles 8. Thus, application of the fluorescent resin 9 onto the LED chip 10 is started (first application process). At this time, it is assumed that the concentration of the fluorescent particles 8 included in the applied fluorescent resin 9 is the first concentration and the amount of the applied fluorescent resin 9 is the first amount. Then, it is assumed that chromaticity of the light-emitting device 2 manufactured by applying onto the LED chip 10 the first amount of the fluorescent resin 9, which includes the fluorescent particles 8 at the first concentration, is the first chromaticity.

In Step S2, it is determined whether or not the time elapsed from the time when the application of the fluorescent resin 9 is started is the predetermined time period (a time which is set beforehand) stored in the storage 3. When the elapsed time is the predetermined time period (Yes in Step S2), the process proceeds to Step S3. When the elapsed time is not the predetermined time period (No in Step S2), application of the fluorescent resin 9 is continued until the elapsed time reaches the predetermined time period.

In Step S3, the concentration of the fluorescent particles 8 included in the fluorescent resin 9 discharged from the applicator 5 is measured by the fluorescent particle measuring apparatus 6 (fluorescent particle measurement process). Specifically, the concentration of the fluorescent particles 8 is measured by performing: a tomographic image obtainment process in which a tomographic image of the applied fluorescent resin 9 is obtained based on the information from the optical coherence tomography unit 17 in FIG. 5; and a first fluorescent particles concentration calculation process in which the concentration of the fluorescent particles 8 included in the fluorescent resin 9 is calculated from the obtained tomographic image.

In Step S4, the fluorescent resin 9 in an amount which corresponds to the concentration of the fluorescent particles 8 measured in Step S3 is applied. For example, it is assumed that the concentration of the fluorescent particles 8 measured in Step S3 is the second concentration and, to manufacture the light-emitting device 2 at the first chromaticity, it is necessary to apply the second amount of the fluorescent resin 9 which includes the fluorescent particles 8 at the second concentration. In this case, the correction apparatus 7 provides the applicator 5 with notification for correction of the application amount so that the applicator 5 applies the second amount of the fluorescent resin 9. Specifically, the applicator 5 applies onto the LED chip 10 the second amount of the fluorescent resin 9. It should be noted that the relationship between the concentration of the fluorescent particles 8, the amount of the fluorescent resin 9, and chromaticity of the light-emitting device 2 is stored in the storage 3 as the reference table. Based on the reference data, the correction apparatus 7 determines the amount of application which allows the manufactured light-emitting devices 2 to have a constant chromaticity, and causes the applicator 5 to apply the fluorescent resin 9 so that the determined application amount is applied.

In Step S5, it is determined whether or not the application to all of the LED chips 10 is completed. When the application is completed (Yes in Step S5), the operation is ended. When the application is not yet completed (No in Step S5), the process returns to Step S2.

As described above, with Step S1 to Step S5, it is possible to reduce occurrence of the variation to chromaticity in manufacturing the light-emitting devices 2.

It should be noted that, after the above-described Step S5, heat is applied so that the fluorescent resin 9 is cured and the LED chip 10 is sealed by the fluorescent resin 9. The light-emitting device 2 is thus manufactured.

Figure 11:
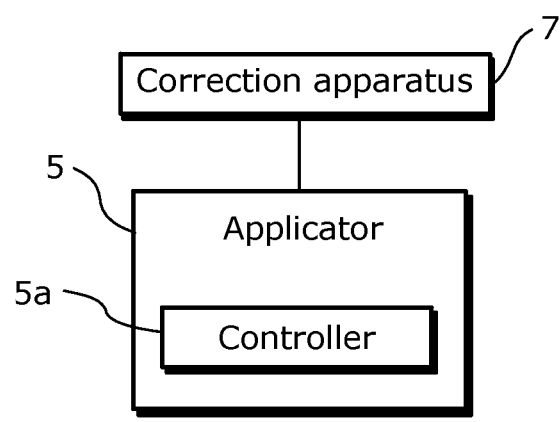
FIG. 11 is a block diagram showing an applicator and a correction apparatus according to the embodiment.

It should be noted that the applicator 5 includes the controller 5a as shown in FIG. 11. The controller 5a performs control, and thereby the amount of the fluorescent resin 9 applied by the applicator 5 is determined. Specifically, in Step S1 in FIG. 6, the applicator 5 is controlled by the controller 5a shown in FIG. 11, and applies the first amount of the fluorescent resin 9. Furthermore, in Step S4 in FIG. 6, the notification for correction from the correction apparatus 7 shown in FIG. 1 is provided to the controller 5a shown in FIG. 11. According to the notification, the controller 5a causes the applicator 5 to apply the second amount of the fluorescent resin 9.

It should be noted that although the optical coherence tomography unit 17 is used as the fluorescent particle measuring apparatus 6, another unit may be used.

Here, another unit used as the fluorescent particle measuring apparatus 6 is described. The another unit (hereinafter referred to as a "transmitted light detection unit") measures the concentration of the fluorescent particles 8 included in the fluorescent resin 9 by using the characteristic that the degree of attenuation (absorbance) of the blue light with the fluorescent particles 8 is proportional to the concentration of the fluorescent particles 8.

Figure 7:
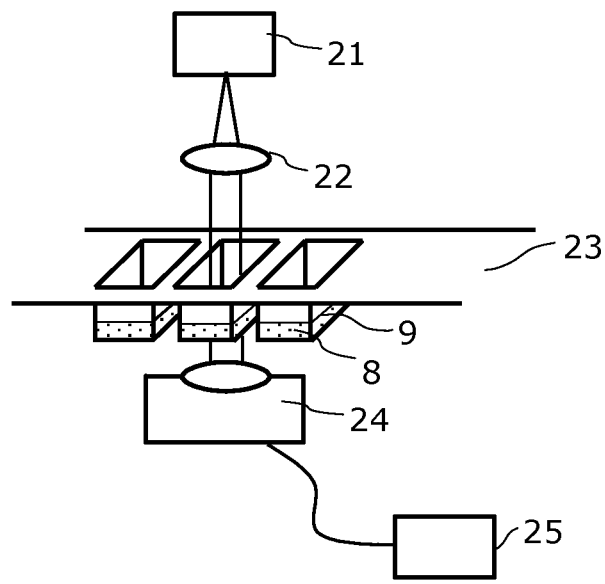
FIG. 7 is a schematic diagram showing another structure of the fluorescent particle measuring apparatus according to the embodiment.

A structure of the transmitted light detection unit is shown in FIG. 7. The transmitted light detection unit includes: a light source 21 which is an emission light source from which measurement light including blue light (wavelength no less than 400 nm and no greater than 500 nm) is irradiated; a collimating lens 22 which convert the measurement light irradiated from the light source 21 into parallel light; a tape 23 which is a transparent member and includes a recess into which the parallel light enters; and a spectroscope 24 into which the transmitted light passed through the recess enters and which disperses the entered transmitted light for each wavelength. Furthermore, the fluorescent resin 9 is applied onto the recess of the tape 23. The measurement light from the light source 21 passes through the recess of the tape 23 onto which the fluorescent resin 9 is applied, and enters the spectroscope 24. Further, the transmitted light detection unit includes a second fluorescent particle concentration calculation unit 25 (a second concentration calculation unit) which calculates, based on an output from the spectroscope 24, the concentration of the fluorescent particles 8 included in the fluorescent resin 9. For the measurement light irradiated from the light source 21, measurement light of a wavelength which excites the fluorescent particles 8 is used. At this time, the measurement light which enters the fluorescent resin 9 is referred to as incident light and the measurement light which passed through the recess is referred to as transmitted light.

Next, the principle of calculation performed by the transmitted light detection unit to obtain the concentration of the fluorescent particles 8 included in the fluorescent resin 9 is described.

Figure 8:
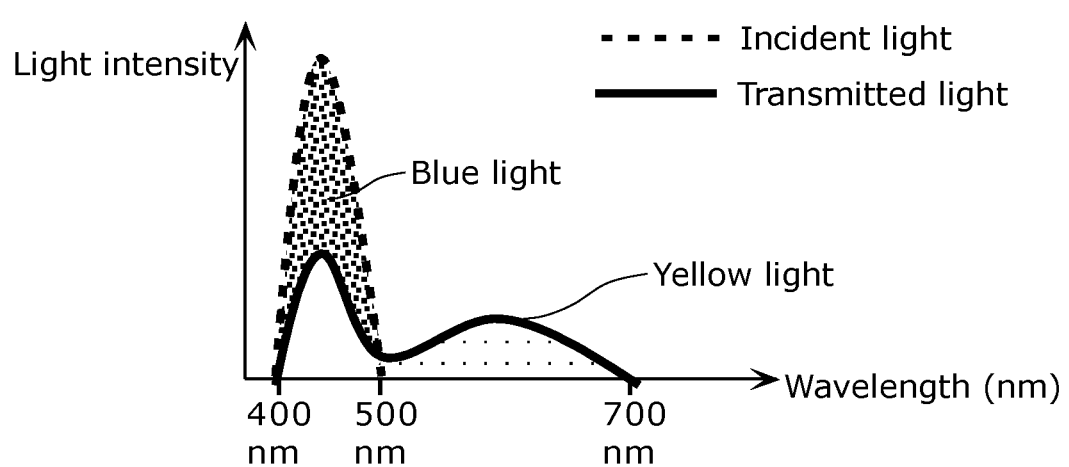
FIG. 8 is a diagram showing a graph which shows an example of optical spectrums of light incident on the fluorescent resin and the light which passed through the fluorescent resin.
Figure 9:
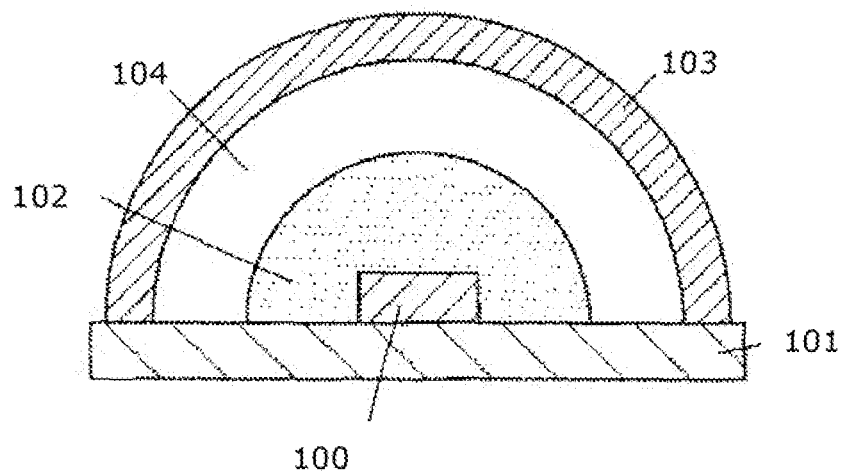
FIG. 9 is a schematic diagram showing a structure of a conventional light-emitting device.
Figure 10:
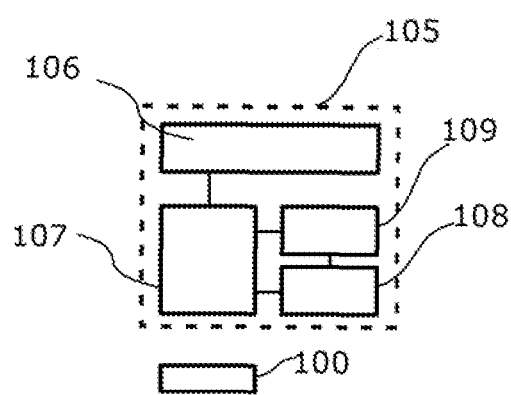
FIG. 10 is a block diagram showing a structure of an apparatus for manufacturing the conventional light-emitting device.

First, an optical spectrum calculated from the transmitted light measured by the spectroscope 24 that is a measuring unit is shown in FIG. 8. In FIG. 8, the horizontal axis indicates a wavelength (nm) and the vertical axis indicates a light intensity. Furthermore, in FIG. 8, the broken line indicates the optical spectrum of the incident light and the solid line indicates the optical spectrum of the transmitted light.

The optical spectrum varies as shown in FIG. 8 between the incident light and the transmitted light. The variation in the optical spectrum is caused by the fluorescent particles 8. Specifically, the light intensity of the blue light is attenuated as the blue light is absorbed by the fluorescent particles 8, and the fluorescent particles 8, which is excited by absorbing the blue light, emits yellow light (wavelength no less than 500 nm and no greater than 700 nm) and thus the light intensity of the yellow light increases.

Based on the variation in the optical spectrum, the concentration of the fluorescent particles 8 is calculated. Here, description is given by using the absorbance of the blue light.

According to the Beer-Lambert law, an absorbance A of the measurement light which enters the fluorescent resin 9 is proportional to a fluorescent particle concentration C and a path length l of the measurement light in the fluorescent resin 9, as shown in (Math. 2).

[Math. 2]

$$A = -\log\left(\frac{I_1}{I_0}\right) = \varepsilon C l \quad \text{(Math. 2)}$$

In the above (Math. 2), $I_0$ represents a light intensity of the incident light, $I_1$ represents a light intensity of the transmitted light, and E represents a molar absorbance coefficient. Here, because ε is a value unique to a substance, these values can be measured beforehand. Furthermore, as the thickness of the fluorescent resin 9, the optical path length l is measured using a laser, image processing, and the like. Further, for $I_0$, a light intensity of the incident light from the light source 21 is measured. For $I_1$, the light intensity of the transmitted light detected by the spectroscope 24 is used. With the above, it is possible to measure the concentration of the fluorescent particles 8 included in the fluorescent resin 9.

It should be noted that the transmitted light detection unit can also detect the light intensity of the yellow light to calculate the concentration of the fluorescent particles 8 which is proportional to the light intensity of the yellow light.

Furthermore, the transmitted light detection unit uses the light which passed through the fluorescent resin 9. Thus, instead of the light-emitting device 2 which includes the package 11 shown in FIG. 2, the fluorescent resin 9 needs to be separately applied onto a transparent member (other than the tape 23 in FIG. 7, glass, a film, or a similar material). Furthermore, as shown in (Math. 2), the thickness of the fluorescent resin 9 is used to calculate the concentration of the fluorescent particles 8. Thus, it is preferable that the thickness of the fluorescent resin 9 be constant. In view of this, after applying the fluorescent resin 9 onto the recess of the tape 23, a transparent member is placed on the fluorescent resin 9 to make the thickness of the fluorescent resin 9 constant. In other words, the applied fluorescent resin 9 is held between the transparent members. It is preferable that the transparent member be glass which has planarity. It should be noted here, "transparent" is defined as a visible light (400 to 700 nm) transmittance rate of 80% or more.

Furthermore, when the thickness of the applied fluorescent resin 9 is increased, detection accuracy of the transmitted light is decreased. Thus, it is preferable that the amount of application be adjusted so that the thickness of the fluorescent resin 9 is 1 mm or less.

It should be noted that the transmitted light detection unit calculates the concentration of the fluorescent particles 8 in Step S3 in the flowchart shown in FIG. 6.

Here, details of the operation performed by the transmitted light detection unit in Step S3 are described using FIG. 1 and FIG. 7.

First, the fluorescent resin 9 discharged from the applicator 5 shown in FIG. 1 is applied onto the tape 23 that is the transparent member (member application process). Next, the fluorescent resin 9 applied onto the tape 23 is irradiated with the measurement light of a wavelength which excites the fluorescent particles 8 by the light source 21 (irradiation process). Subsequently, the spectroscope 24 that is the measuring unit measures the light intensity of the measurement light (transmitted light) which passed through the fluorescent resin 9 (measurement process). Lastly, based on the light intensity of the measured transmitted light, the second fluorescent particle concentration calculation unit 25 calculates the concentration of the fluorescent particles 8 included in the fluorescent resin 9 (second fluorescent particle concentration calculation process).

It should be noted that the transmitted light detection unit calculates the concentration of the fluorescent particles 8 based on the actual emission of light, and thus can calculate the concentration of the fluorescent particles 8 with high precision as compared to the case in which the optical coherence tomography unit 17 is used. On the other hand, when the optical coherence tomography unit 17 is used, concentration of the fluorescent particles 8 can be measured at high speed because the additional application of the fluorescent resin 9 to the transparent member, which is required by the transmitted light detection unit, is not necessary.

It should be noted that if, for example, the concentration of the fluorescent particles 8 included in the fluorescent resin 9 discharged from the applicator 5 is measured in the air, a transparent member such as the tape 23 is not necessary. However, use of the tape 23 or a similar material makes it possible to measure the concentration with high precision.

As described above, with the manufacturing apparatus 1, it is possible to prevent the occurrence of variation to chromaticity of the manufactured light-emitting device.

It should be noted that the present invention is not limited to the above embodiment. For example, another embodiment realized by arbitrarily combining components which are described in this description and another embodiment realized by removing some components may be embodiments of the present invention. Furthermore, the present invention also includes modifications obtained by applying, to the above-described embodiments, various changes that can be conceived by a person skilled in the art without departing from the scope of the present invention which is the meaning indicated by words described in the claims.

For example, in the embodiment described above, the correction apparatus 7 notifies the applicator 5 of the application amount based on the information in Table 1 stored in the storage 3. However, alternatively, the storage 3 may store the linear function shown in FIG. 4, and, based on the function, the correction apparatus 7 may notify the applicator 5 of the application amount of the fluorescent resin 9.

INDUSTRIAL APPLICABILITY

The present invention can be applied to LEDs, and also to plasma displays and the like that are devices manufactured by applying fluorescent substances.

REFERENCE SIGNS LIST

1 Manufacturing apparatus
2 Light-emitting device
3 Storage
5 Applicator
6 Fluorescent particle measuring apparatus
7 Correction apparatus
8 Fluorescent particles
9 Fluorescent resin
10 LED chip
17 Optical coherence tomography unit
18 First fluorescent particle concentration calculation unit
20 Tomographic image obtaining unit
21 Light source
23 Tape
25 Second fluorescent particle concentration calculation unit

The invention claimed is:

1. An apparatus for manufacturing a light-emitting device by applying, onto a light-emitting source, a fluorescent resin which includes fluorescent particles and is stored in and discharged from an applicator, the apparatus comprising:
a controller programmed to control an application amount of the fluorescent resin that is discharged from the applicator;
a fluorescent particle measurer configured to measure a first concentration that is a number concentration of the fluorescent particles included in the fluorescent resin discharged from the applicator by counting the fluorescent particles included in the fluorescent resin discharged from the applicator;

a storage in which reference data is stored beforehand, the reference data indicating a relationship between a number concentration of the fluorescent particles and an application amount of the fluorescent resin that enables the light-emitting device to have constant chromaticity; and a corrector which determines, based on the first concentration and the reference data, a corrected application amount of the fluorescent resin to be applied onto the light-emitting source and notifies the controller of the corrected application amount.

2. The apparatus according to claim 1, wherein the fluorescent particle measurer includes:

an optical coherence tomograph which obtains a tomographic image of the fluorescent resin discharged from the applicator; and a first concentration calculator which calculates the first concentration based on the tomographic image.

3. The apparatus according to claim 1, wherein the fluorescent particle measurer measures the first concentration at predetermined time intervals.

* * * * *